US005789234A

United States Patent [19]
Bertelsen et al.

[11] Patent Number: 5,789,234
[45] Date of Patent: Aug. 4, 1998

[54] EXPRESSION SYSTEMS FOR AMIDATING ENZYME

[75] Inventors: Arthur H. Bertelsen, Teaneck; Nozer M. Mehta, Rockaway; Gary Agide Beaudry, Montclaire; James P. Gilligan, Union, all of N.J.; Barry N. Jones, Wayne, Pa.

[73] Assignee: Unigene Laboratories, Inc., Fairfield, N.J.

[21] Appl. No.: 307,366

[22] Filed: Feb. 6, 1989

Related U.S. Application Data

[63] Continuation-in-part of Ser. No. 86,161, Aug. 14, 1987.
[51] Int. Cl.$^6$ .............. C12N 5/10; C12N 15/63; C12N 1/21; C07H 21/04
[52] U.S. Cl. ............... 435/240.2; 435/320.1; 435/252.3; 536/23.2
[58] Field of Search .................. 435/320, 243, 435/172.3, 240.1, 228, 320.1, 240.2, 252.3; 536/27, 23.2

[56] References Cited

U.S. PATENT DOCUMENTS

| | | | |
|---|---|---|---|
| 4,708,934 | 11/1987 | Gilligan | 435/68 |
| 4,921,797 | 5/1990 | Matsuo, et al. | |

FOREIGN PATENT DOCUMENTS

| | | |
|---|---|---|
| 133 282 | of 0000 | European Pat. Off. |
| 134 631 | of 0000 | European Pat. Off. |
| 197 794 | of 0000 | European Pat. Off. |
| 299790 | of 0000 | European Pat. Off. |
| 90 30 1034 | of 0000 | European Pat. Off. |
| 249477 | 12/1987 | European Pat. Off. |
| 308067 | 3/1989 | European Pat. Off. |
| 62-177184 | of 0000 | Japan |
| 62-306867 | of 0000 | Japan |
| WO 8602099 | of 0000 | WIPO |
| WO 89/02460 | of 0000 | WIPO |
| WO 90/08194 | of 0000 | WIPO |
| WO8902460 | of 0000 | WIPO |
| WO 9008190 | 7/1990 | WIPO |

OTHER PUBLICATIONS

Murthy et al., "Purification and Characterization of Peptidylglycine . . . ", pp. 1815–1822, Feb. 6, 1986.
Husain et al., "Formation of the COOH–terminal amide group of thyrotropin–releasing–factor", pp. 277–281, Feb. 1983.
Glembotski et al., "Characterization of a Peptide α–Amidation Activity . . . ", pp. 6385–6392, May 25, 1984.
Bradbury et al., "Mechanism of C–terminal amide formation by pituitary enzymes", pp. 686–688, Aug. 12, 1982.
Eipper et al., "Bovine Intermediate Pituitary α–Amidation Enzyme: Preliminary Characterization", pp. 921–928 (1983).
Eipper et al., Mole. Endo., vol. 1, pp. 777–790, (1987), "Structure of the Precursor to an Enzyme Mediating . . . ".
Hsueh, "Proteases In Hormone Production and Metabolism", pp. 141–151.

Amara et al., Proc. Natl. Acad. Sci., vol. 77, pp. 4444–4448, 1980.
Perkins, et al., Mole. Endo., vol. 4, pp. 132–139 (1990), "Stable Expression of Full–Length and Truncated Bovine . . . ".
Stoffers, et al., Proc. Natl. Acad. Sci., vol. 86, pp. 735–739 (1989), "Alternative mRNA splicing generates multiple . . . ".
Glauder, et al., Biochem. and Biophys. Rsrch. Comm., vol. 169, pp. 551–558 (1990, "Human Peptidylglucine alpha . . . ".
Ouafik, et al., Journal of Bio. Chem., vol.264, pp.5839–5845 (1989), "Developmental Regulation of Peptidylglycine . . . ".
Thiele et al., Endocrinology, vol.125, pp.2279–2288 (1989), "Tissue–Specific Regulation of Peptidyl–Glycine . . . ".
Noguchi, et al. Archives of Biochem. and Biophys., vol. 275, pp. 505–513 (1989), "Rat Peptidylglucine alpha . . . ".
Stoffers, et al., Adv. Gene Tech., vol. 9, p. 120 (1989), "Multiple Forms of Rat Peptidylglycine Alpha–Amidating . . . ".
Braas, et al., Molecular Endocrinology, vol. 3, pp.1387–1398 (1989) "Tissue Specific Expression of Rat Peptidyl . . . ".
Ohsuye, et al., Cloning of cDNA Encoding a New Peptide C–Terminal Alpha–Amidating Enzyme . . . pp.1275–1281, Feb. 15, 1988.
Mizuno, et al., Peptide C–Terminal Alpha–Amidating Enzyme Purified to Homogeneity . . . pp.984–991, Jun. 30, 1986.
Mizuno, et al., Cloning and Sequence of cDNA Encoding a Peptide C–Terminal . . . pp.546–552, Oct. 29, 1987.
Stoffers, et al., Alternative mRNA Splicing Generates Multiple Forms of Peptidyl–Glycine . . . pp. 735–739, Jan. 1989.
Mehta, et al., Purification of a Peptidylglycine Alpha–Amidating Enzyme . . . pp. 44–54, Feb. 15, 1988.
Tamburini, et al., Structure–Activity Relationships For Glycine–Extended Peptides . . . Dec., pp. 623–631, 1988.
Eipper, et al., "Membrane–Associated Peptidylglycine Alpha–Amidating Monooxygenase in the Heart", Jun. 15, 1988, pp.8371–8379.
Eipper, et al., Structure of the Precursor to an Enzyme Mediating COOH Terminal . . . pp. 777–790, 1987.
Bradbury, et al., "Peptide Amidation: Evidence for Multiple Molecular Forms of the Amidating . . . ", pp.1293–1300, Aug. 15, 1988.
Murthy et al. "Purification & characterization of PAN from . . ." JBC 261, 1815–1822, 1986.

Primary Examiner—George C. Elliott
Attorney, Agent, or Firm—Ostrolenk, Faber, Gerb & Soffen, LL

[57] ABSTRACT

Alpha-amidating enzyme is produced by recombinant DNA techniques recoverable in high yields and at high purity. Both eukaryotic and prokaryotic expression vectors are provided having a transcriptional promoter followed downstream by a DNA sequence which encodes amidating enzyme. The vector selected is one capable of directing the expression of polypeptides in the host selected, and preferred hosts are transfected with the described vectors.

38 Claims, 15 Drawing Sheets

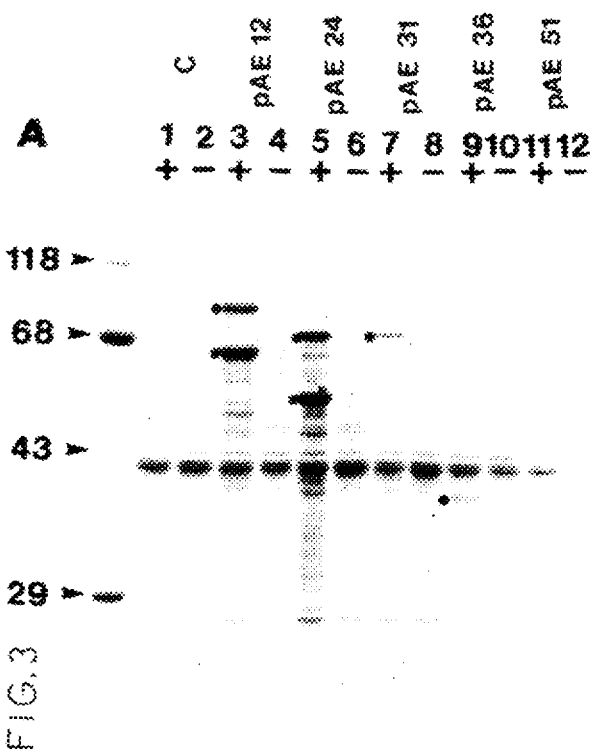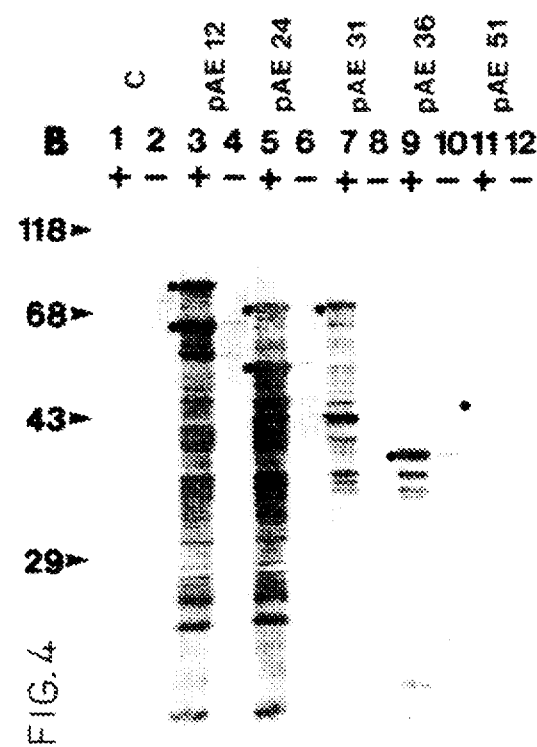

α-AE Type A Composite  FIG. 5A

```
-345
GGGATGCTGTGCCAGTGGGACCAGGTTCCGAATGATGACTGCCGAATTGCCGAGCGATAAGGACCCTGCTCC
                                                                        -246
TCCAGCCCTGTGGCTGCCACCGGTCTCGGCCGTCTCGGAGGGCGGGCTCCAGAGCCGCTTCCCACGGTCGGA
                                                                        -146
GCGGACGGAGCGGACCCGGCTGGCCGCGCATCGCCCCTCGCCCCGGCCCCGCCGGCCCGCCCAGCCTGCCA
                                                                        -46
TCCCGCGGCCACTGCCGCTGCCCCTGGTCTCGCCCTGCGGGACATGGGCCCGCCAGCGGTCTGCTACTGCTGTGGGGCTGCTCGCCC
                                                                        55
                              M  A  G  R  A  R  S  G  L  L  L  L  L  G  L  L  L  A
                                                                        (18)
TGCAGAGCAGCTGCCTGGCCTTCAGAAGCCCACTTTCTGTCTTTAAGAGGTTTAAAGAAACTACCAGATCATTTTCCAATGAATGCCTTGGTACCATTGG
                                                                        155
 L  Q  S  S  C  L  A  F  R  S  P  L  S  V  F  K  R  F  K  E  T  T  R  S  F  S  N  E  C  L  G  T  I  G
                                                                        (52)
ACCAGTCACCCCTCTTGATGCATCAGATTTTGCGCTGGATATTCGCATGCCTGGGGTTACACCTAAAGAGTCTGACACATACTTCTGCATGTCCATGCGT
                                                                        255
 P  V  T  P  L  D  A  S  D  F  A  L  D  I  R  M  P  G  V  T  P  K  E  S  D  T  Y  F  C  M  S  M  R
                                                                        (85)
CTGCCTGTGGATGAGGAAGCCTTCGTGATTGACTTCAAGCCTCGTGCCAGCATGGATACTGTCCACCATATGCTGCTGTTTGGATGCAATATGCCCTCGT
                                                                        355
 L  P  V  D  E  E  A  F  V  I  D  F  K  P  R  A  S  M  D  T  V  H  H  M  L  L  F  G  C  N  M  P  S
                                                                        (118)
```

FIG. 5B

```
CCACTGGAAGTTACTGGTTTTGTGATGAAGGAACCTGTACAGATAAAGCCAATATTCTATATGCCTGGGCAAGGAATGCTCCCCACCGGCTCCCGAA    455
 S  T  G  S  Y  W  F  C  D  E  G  T  C  T  D  K  A  N  I  L  Y  A  W  A  R  N  A  P  P  T  R  L  P  K   (152)

AGGTGTTGGATTCAGAGTTGGAGGAGAAACTGGAAGCAAATACTTCGTCCTTCAAGTTCACTATGGCGATATCAGTGCTTTTCGAGATAATCACAAAGAC    555
 G  V  G  F  R  V  G  G  E  T  G  S  K  Y  F  V  L  Q  V  H  Y  G  D  I  S  A  F  R  D  N  H  K  D    (185)

TGCTCTGGCGTGTCCGTACATCTCACACGTGTGCCCCAGCCTTTAATTGCGGGCATGTACCTTATGATGTCTGTTGACACTGTCATACCACCAGGAGAGA    655
 C  S  G  V  S  V  H  L  T  R  V  P  Q  P  L  I  A  G  M  Y  L  M  M  S  V  D  T  V  I  P  P  G  E    (218)

AAGTAGTGAATGCTGACATTTCGTGCCAATACAAAATGTATCCAATGCATGTGTTTGCCTACAGAGTCCACACTCACCATTTAGGTAAGGTGGTGAGCGG    755
 K  V  V  N  A  D  I  S  C  Q  Y  K  M  Y  P  M  H  V  F  A  Y  R  V  H  T  H  H  L  G  K  V  V  S  G   (252)

ATACAGAGTAAGAAACGGACAGTGGACACTGATTGGACGGCCAGAACCCCAGCTGCCACAGGCTTTCTACCCTGTGGAACACCCCGTTGATGTTACTTTT    855
 Y  R  V  R  N  G  Q  W  T  L  I  G  R  Q  N  P  Q  L  P  Q  A  F  Y  P  V  E  H  P  V  D  V  T  F    (285)
```

FIG. 5C

```
GGTGATATACTGGCAGCCAGATGTGTTCACTGGTGAAGGGAGGACAGAGGCCACCCATATCGGCGGCACTTCTAGTGACGAAATGTGTAACCTGTACA    955
 G  D  I  L  A  A  R  C  V  F  T  G  E  G  R  T  E  A  T  H  I  G  G  T  S  S  D  E  M  C  N  L  Y   (318)

TCATGTATTACATGGAAGCCAAATATGCACTTTCCTTCATGACCTGTACAAAGAACGTGGCTCCAGATATGTTCAGAACTATCCCAGCAGAGGCCAATAT   1055
 I  M  Y  Y  M  E  A  K  Y  A  L  S  F  M  T  C  T  K  N  V  A  P  D  M  F  R  T  I  P  A  E  A  N  I  (352)

CCCAATTCCTGTCAAACCGGACATGGTTATGATGCACGGCATCACAGAAGCAGAAAACAAGAAGAGTGCTTTAATGCAGCAGCCAAAACAGGGA   1155
 P  I  P  V  K  P  D  M  V  M  M  H  G  H  H  K  E  A  E  N  K  E  K  S  A  L  M  Q  Q  P  K  Q  G   (385)

GAGGAAGAAGTATTAGAGCAGGATTTCCATGTGGAAGAAGAACTGGACTGGCCTGGAGTGTACTTGTTACCAGGCCAGGTTTCTGGGGTGGCCCTGGATT   1255
 E  E  E  V  L  E  Q  D  F  H  V  E  E  E  L  D  W  P  G  V  Y  L  L  P  G  Q  V  S  G  V  A  L  D   (418)

CTAAGAATAACCTAGTGATTTTCCACAGAGGTGACCATGTTTGGGATGGAAACTCTTTTGACAGCAAGTTGTTTACCAGCAAAGAGGTCTTGGGCCAAT   1355
 S  K  N  N  L  V  I  F  H  R  G  D  H  V  W  D  G  N  S  F  D  S  K  F  V  Y  Q  Q  R  G  L  G  P  I  (452)
```

FIG. 5D

```
TGAAGAAGACACCACCATCCTGGTCATTGACCCAAATAATGCTGAAATCCTCCAGTGGCAAGAACCTGTTTTATTACCACACGGGCTTGAGCATAGAT   1455
 E  E  D  T  I  L  V  I  D  P  N  N  A  E  I  L  Q  S  S  G  K  N  L  F  Y  L  P  H  G  L  S  I  D   (485)

ACAGATGGAAATTATTGGGTCACAGATGTGGCTCTCCACCAGGTGTTCAAATTGGACCCGCATAGCAAGGAAGGCCCTCTCTTAATTCTGGGAAGGAGCA   1555
 T  D  G  N  Y  W  V  T  D  V  A  L  H  Q  V  F  K  L  D  P  H  S  K  E  G  P  L  L  I  L  G  R  S   (518)

TGCAACCTGGGAGTGACCAAAACCATTTCTGCCAGCCCAGTACTGGAGCTGTCTTCGTGTCAGACGGGTTACTGTAACAG                      1655
 M  Q  P  G  S  D  Q  N  H  F  C  Q  P  T  D  V  A  V  E  P  S  T  G  A  V  F  V  S  D  G  Y  C  N  S (552)

TCGGATTGTGCAGTTTTCACCAAGCGGAAAGTTCGTCACCCAGTGGGAGAAGAGTCCTCTGGAAGCAGTCCTAGGCCAGGCCAGTTCAGTGTTCCTCAC   1755
 R  I  V  Q  F  S  P  S  G  K  F  V  T  Q  W  G  E  E  S  S  G  S  S  P  R  P  G  Q  F  S  V  P  H   (585)

AGTTTGGCCCTTGTGCCTCATTTGGACCAGTTGTGTGTGGCAGACAGGGAAAATGGCCGAATCCAATGCTTCAAAACTGACACCAAAGAATTTGTGAGAG   1855
 S  L  A  L  V  P  H  L  D  Q  L  C  V  A  D  R  E  N  G  R  I  Q  C  F  K  T  D  T  K  E  F  V  R   (618)
```

FIG. 5E

```
AGATTAAGCACGCATCATTTGGAAGGAATGTCTTTGCCATTTCATATACCAGTTTCCTCTTTGCCGTAAACGGGAAGCCTTACTTTGGAGACCAAGA    1955
 E  I  K  H  A  S  F  G  R  N  V  F  A  I  S  Y  I  P  G  F  L  F  A  V  N  G  K  P  Y  F  G  D  Q  E   (652)

GCCCGTGCAAGGATTGTGATGAACTTTTCCAGTGGGGAAATTATAGACGTCTTCAAGCCAGTACGCAAGCACTTCGACATGCCTCATGATATTGTGCT    2055
 P  V  Q  G  F  V  M  N  F  S  S  G  E  I  I  D  V  F  K  P  V  R  K  H  F  D  M  P  H  D  I  V  A   (685)

TCTGAAAGATGGGACTGTGTATACATTGGAGACGCACACACAAACACCCTGTGAACCAAAGTTCACCCTGAAAAAATGGAGCATCGGTCAGTTAAAAAGGCTG    2155
 S  E  D  G  T  V  Y  I  G  D  A  H  T  N  T  V  W  K  F  T  L  T  E  K  M  E  H  R  S  V  K  K  A   (718)

GCATTGAAGTCCAGGAGAAATCAAGGACCCGGCTCGGGAGTGTCCGTGGTTCTCATTACAACCCTCTGGTTATTCCTGTGCTGGCCATTGTCATGTTTATT    2255
 G  I  E  V  Q  E  I  K  E  A  A  V  V  E  P  K  V  E  N  K  P  T  S  S  E  L  Q  K  M  Q  E  K  Q   (752)

GAAACTGAGCACAGAGAGGCCCGGCTCGGGAGTGTCCGTGGTTCTCATTACAACCCTCTGGTTATTCCTGTGCTGGCCATTGTCATGTTTATT    2355
 K  L  S  T  E  P  G  S  G  Y  S  V  V  L  I  T  T  L  L  V  I  P  V  L  L  A  I  V  M  F  I   (785)

CGGTGGAAAAATCAAGGGCCTTTGGAGGAGGAAAAGCGGAAGGAAGCGGCAGGGCTTAAATTTCTTTGCAAGTCGAAAAGGCTACAGCAGAAAGGGTTTG    2455
 R  W  K  K  S  R  A  F  G  G  K  G  S  G  G  L  N  L  G  N  F  F  A  S  R  K  G  Y  S  R  K  G  F   (818)

ACCGAGTGAGCACAGAGGGGAGTGACCAAGAGAGAAAGATGAGGAAGTGAGTCTGAAGAGAGAGTACTCGGCCCCCGTGCCCAAGCTTGCACCTTC    2555
 D  R  V  S  T  E  G  S  D  D  E  K  D  E  D  D  G  S  E  E  E  Y  S  A  P  L  P  K  P  A  P  S   (852)

CTCCTGAGCTCCAGCCTTCGCCCGGGTAGCAGCTGGACTGAGGTTACCAGGATGCCCAGACTCCTCCCCTTTAGCGCGTGTAAAGTTCTGTGCATTTGATT    2655
 S                                                                                                     (853)
```

FIG. 5F

```
GTAAACTGTACTCGTCAGTGTGGGACTGTACACACCTTTATTACTTCATTTGGCTCCGTTGGCTTCTGTTTTCTAGGTGAGGAGTTCCCACCAGTTCA    2755

CTCCAGTGCCATTGTCTTTATATGAACTTAGCGTAGAGACCGCCCTTCCTCTTCCAAGGTACGGTCACCCGAGGAAGTTAGCTCATTCACATTGAGAC    2855

GTTAGTTGGGATGTAAATAGCCCTATTCTCTGCTTGAACACAGTATTCTCCCAGTCCACACCCATCGCCAGTGTCTTTCTTTGGTGCCTTTCCTGTTC    2955

AGCATTCTCAGCCTGTGGCAGTGAAGAGAACCAACCTGCCACACGACGAAAAGTCGCTAAATCTCTTCTATTTTTTAAAATCACTAACATTATATGCA    3055

ATGAGAGAAATTTTAAAAGTCTCTATTTAAATTCTTTTTTTTAAATTCTCTCCTCAGTTGGTGTGTTTCCGGGATGTCTTATTTTTTAGATGGTTACACT    3155

GTTAGAACACTATTTTTCAGAATCTGAATGTAATAAAGTGTTTCAGAGCATTACGAAAAAAAAAAAAAAAAAA
                                        3214
```

α-AE Type B Composite    FIG. 6A

```
-345
GGGATGCTGCCAGTGGGACCAGGTTCCGAATGATGACTGCCGCGGGTCTGCCGCGATAGCCCTCACAGCCCTGCCGGCATTGCGAGCGATAAGGACCCTGCTCC    -246
TCCAGCCCTGTGCCTGCCACCGGCTCTGGCCGCGCTCTGGAGGGCGGCGGCGGCGGCGGAGCGGCGGCGGACTCCAGAGAGCCGCCTTCCCACGCGTCGGGA    -146
GCGGACGGAGCGGAGACCGGCTGGCGCGCATCGCCCTCGCGCCCAGCCCTGCCGCCATGAAGTAGCTGCCCCGCCGGCCCGCCCAGCCCTGCCA    -46
TCCCGCCGGCCCCGGCCACTGCCTGCCCCTGCCCTGGTCCTGCCGGACATGGCCGGACGCGCCAGCGGTCTGCTACTGCTGCTGCTGGGGCTGCTCGCCC    55
                                                    M  A  G  R  A  R  S  G  L  L  L  L  L  G  L  L  A    (18)
TGCAGAGCAGCTGCCTGGCCTTCAGAAGCCCACTTTCTGTCTTTAAGAGGTTTAAAGAAACTACCAGATCATTTTCCAATGAATGCCTTGGTACCATTGG    155
 L  Q  S  S  C  L  A  F  R  S  P  L  S  V  F  K  R  F  K  E  T  T  R  S  F  S  N  E  C  L  G  T  I  G    (52)
ACCAGTCACCCCTCTTGATGCATCAGATTTTGCGCTGGATATTCGCATGCCTGGGGTTACACCTAAAGAGTCTGACACATACTTCTGCATGTCCATGCGT    255
 P  V  T  P  L  D  A  S  D  F  A  L  D  I  R  M  P  G  V  T  P  K  E  S  D  T  Y  F  C  M  S  M  R    (85)
CTGCCTGTGGATGAGGAAGCCTTCGTGATTGACTTCAAGCCTCGTGCCAGCATGGATACTGTCCACCATATGCTGTTTGGATGCAATATGCCCTCGT    355
 L  P  V  D  E  E  A  F  V  I  D  F  K  P  R  A  S  M  D  T  V  H  H  M  L  F  G  C  N  M  P  S    (118)
```

FIG. 6B

```
CCACTGGAAGTTACTGGTTTTGTGATGAAGGAACCTGTACAGATAAAGCCAATATTCTATATGCCTGGGCAAGGAATGTCTCCCCACCCGGCTCCCGAA    455
 S  T  G  S  Y  W  F  C  D  E  G  T  C  T  D  K  A  N  I  L  Y  A  W  A  R  N  A  P  P  T  R  L  P  K   (152)

AGGTGTTGGATTCAGAGTTGGAGGAGAAACTGGAAGCAAATACTTCGTCCTTCAAGTTCACTAGGCGATATCAGTGCTTTTCGAGATAATCACAAAGAC    555
 G  V  G  F  R  V  G  G  E  T  G  S  K  Y  F  V  L  Q  V  H  Y  G  D  I  S  A  F  R  D  N  H  K  D   (185)

TGCTCTGGGGTGTCCGTACATCTCACACGTGTGCCCCAGCCTTTAATTGCGGGCATGTACCTTATGATGTCTGTTGACACTGTCATACCACCAGGAGAGA    655
 C  S  G  V  S  V  H  L  T  R  V  P  Q  P  L  I  A  G  M  Y  L  M  M  S  V  D  T  V  I  P  P  G  E   (218)

AAGTAGTGAATGCTGACATTTCGTGTCAATACAAAATGTATCCAATGCATGTGTTTGCCTACAGAGTCCACACTCACCATTTAGGTAAGGTGGTGAGCGG    755
 K  V  V  N  A  D  I  S  C  Q  Y  K  M  Y  P  M  H  V  F  A  Y  R  V  H  T  H  H  L  G  K  V  V  S  G   (252)

ATACAGAGTAAGAAACGGACAGTGGACACTGATTGGACGCCAGAACCCCCAGCTGCCACAGGCTTTCTACCCTGTGGAACACCCCGTTGATGTTACTTTT    855
 Y  R  V  R  N  G  Q  W  T  L  I  G  R  Q  N  P  Q  L  P  Q  A  F  Y  P  V  E  H  P  V  D  V  T  F   (285)
```

FIG.6C

```
GGTGATATACTGGCAGCCAGATGTGTGTTCACTGGTGAAGGGAGGAGGACAGAGGCCACCCACATCGGCGGCACTTCTAGTGACGAAATGTGTAACCTGTACA    955
 G  D  I  L  A  A  R  C  V  F  T  G  E  G  R  T  E  A  T  H  I  G  G  T  S  S  D  E  M  C  N  L  Y       (318)
TCATGTATTACATGGAAGCCAAATATGCACTTTCCTTCATGACCTGTACAAAGAACGTGGCTCCAGATATGTTCAGAACTATCCCAGCAGAGGCCAATAT     1055
 I  M  Y  Y  M  E  A  K  Y  A  L  S  F  M  T  C  T  K  N  V  A  P  D  M  F  R  T  I  P  A  E  A  N  I    (352)
CCCAATTCCTGTCAAACCGGACATGGTTATGATGCACGGGCATCACAAAGAAGCAGAAAACAAAGAGTGCTTTAATGCAGCAGCCAAAACAGGGA           1155
 P  I  P  V  K  P  D  M  V  M  M  H  G  H  H  K  E  A  E  N  K  E  K  S  A  L  M  Q  Q  P  K  Q  G       (385)
GAGGAAGAAGTATTAGAGCAGGGTGATTTCTATTCACTGCTTTCCAAGCTGCTAGGAGAAAGGGAAGATGTTCATGTGCACAAGTATAATCCTACAGAAA     1255
 E  E  E  V  L  E  Q  G  D  F  Y  S  L  L  S  K  L  L  G  E  R  E  D  V  H  V  H  K  Y  N  P  T  E       (418)
AGACAGAATCTGGGGTCAGACCTGGTAGCTGAGATTGCAAACGTGGTCCAGAAAAAGGACCTTGGTCGGTCTGACGCCAGAGAAGGTGCAGAGCATGAGGA    1355
 K  T  E  S  G  S  D  L  V  A  E  I  A  N  V  V  Q  K  K  D  L  G  R  S  D  A  R  E  G  A  E  H  E  E    (452)
```

FIG. 6D

```
ATGGGGTAATGCTATCCTAGTCAGAGACAGGATCCACCAGATTCCACAGATTCCAGAGTCAACTCTGAGGCCAGCTGAGAGCAGAGCTTTCTCGTTCCAGCAG  1455
 M  G  N  A  I  L  V  R  D  R  I  H  R  F  H  Q  L  E  S  T  L  R  P  A  E  S  R  A  F  S  F  Q  Q   (485)

CCTGGGCGAAGGCCCTTGGGAACCAGAACCCTCAGGAGATTTCCATGTGGAAGAACTGGACTGGCCTGGAGTGTACTTGTTACCAGGCCAGGTTTCTG  1555
 P  G  E  G  P  W  E  P  E  P  S  G  D  F  H  V  E  E  E  L  D  W  P  G  V  Y  L  L  P  G  Q  V  S   (518)

GGGTGGCCCTGGATTCTAAGAATAACCTAGTGATTTTCCACAGAGGTGACCATGTTTGGGATGGAAACTCTTTTGACAGCAAGTTTGTTACCAGCAAAG  1655
 G  V  A  L  D  S  K  N  N  L  V  I  F  H  R  G  D  H  V  W  D  G  N  S  F  D  S  K  F  V  Y  Q  Q  R  (552)

AGGTCTTGGGCCAATTGAAGAGACACCATCCTGGTCATTGACCCAAATAATGCTGAAGAACCTGTGTTTATTTACCACAC  1755
 G  L  G  P  I  E  E  D  T  I  L  V  I  D  P  N  N  A  E  I  L  Q  S  S  G  K  N  L  F  Y  L  P  H  (585)

GGCTTGAGCATAGATACAGATGGAAATTATTGGGTCACAGATGTGGCTCTCCCACCAGGTGTTCAAATTGGACCCGCATAGCAAAGAAGGCCCTCTCTTAA  1855
 G  L  S  I  D  T  D  G  N  Y  W  V  T  D  V  A  L  H  Q  V  F  K  L  D  P  H  S  K  E  G  P  L  L   (618)
```

FIG. 6E

```
TTCTGGAAGGAGCATGCAACCTGGGAGTGACCAAAATCATTTCTGCCAGCCCCACCGATGTGGCTGTGGAGCCCAGTACTGGAGCTGTCTTCGTGTCAGA   1955
 I  L  G  R  S  M  Q  P  G  S  D  Q  N  H  F  C  Q  P  T  D  V  A  V  E  P  S  T  G  A  V  F  V  S  D   (652)
CGGTTACTGTAACAGTCGGATTGTGCAGTTTTCACCCAAGGCGGAAAGTTCGTCACCCAGTGGGGAGAAGAGTCCTCTGGAAGCAGTCCTAGGCCAGGCCAG   2055
 G  Y  C  N  S  R  I  V  Q  F  S  P  S  G  K  F  V  T  Q  W  G  E  E  S  S  G  S  S  P  R  P  G  Q    (685)
TTCAGTGTTCCTCACAGTTTGGCCCTTGTGCCTCATTTGGACCAGTTGTGTGTGGCAGACAGGGAAAATGGCCGAATCCAAAACTGACACCA   2155
 F  S  V  P  H  S  L  A  L  V  P  H  L  D  Q  L  C  V  A  D  R  E  N  G  R  I  Q  C  F  K  T  D  T   (718)
AAGAATTGTGAGAGAGATTAAGCACGCATCATTGGAAGGAATGTCTTTGCCATTTCATATATACCAGGTTTCTCTTTGCCGTAAACGGGAAGCCTTA   2255
 K  E  F  V  R  E  I  K  H  A  S  F  G  R  N  V  F  A  I  S  Y  I  P  G  F  L  F  A  V  N  G  K  P  Y   (752)
CTTTGGAGACCAAGAGCCCGTGCAAGGATTTGTGATGAACTTTTCCAGTGGGAAATTATAGACGTCTTCAAGCCAGTACGCAAGCACTTCGACATGCCT   2355
 F  G  D  Q  E  P  V  Q  G  F  V  M  N  F  S  S  G  E  I  I  D  V  F  K  P  V  R  K  H  F  D  M  P   (785)
```

FIG. 6F

```
CATGATATTGTGGCTTCTGAAGATGGGACTGTGTACATTGGAGACGCACACAAACCGTGTGGAAGTTCACCCTGACTGAAAAAATGGAGCATCGGT    2455
 H  D  I  V  A  S  E  D  G  T  V  Y  I  G  D  A  H  T  N  T  V  W  K  F  T  L  T  E  K  M  E  H  R      (818)

CAGTCAAAAAGGCTGGCATTGAAGTCCAGGAAATCAAAGCCGAGGCAGTTGTTGAACCCAAAGTGGAGAACAAACCCACCTCCTCAGAATTGCAGAAGAT    2555
 S  V  K  K  A  G  I  E  V  Q  E  I  K  A  E  A  V  V  E  P  K  V  E  N  K  P  T  S  S  E  L  Q  K  M    (852)

GCAAGAGAAACAGAAACTGAGCACAGAGCCCGGCTCGGGAGTGTCCGTGGTTCTCATTACAACCCTTCTGGTTATTCCTGTGCTGGTCCTGCTGGCCATT    2655
 Q  E  K  Q  K  L  S  T  E  P  G  S  G  V  S  V  V  L  I  T  T  L  L  V  I  P  V  L  V  L  L  A  I      (853)

GTCATGTTTATTCGGTGGAAAAATCAAGGGCCTTTGGAGCAGATCATGACCGCAAGTCGAGTCCTGGGAAGAGAAGAGGAG    2755
 V  M  F  I  R  W  K  K  S  R  A  F  G  A  D  H  D  R  K  L  E  S  S  G  R  V  L  G  R  R  G  G         (886)

GAAGAGAAGAAGAAGAAGAGAGAAGGAGAAAAGCAGAAGAAGAAAAAGCAGAAGAAGGGCAGCATTAGCCATGGGC    2855
 G  G  R  R  E  G  G  R  G  R  E  G  G  R  K  A  E  G  G  R  R  G  E  G  G  R                           (912)

AGGGCTCTGAGAATAAGTAGAAGGGGAAAGGGATTGGCTAAGCACCGATTCAAAGCTGTCAGTCCTTTGGGCTGCAGATGCAATGTGGCT    2945
 G  G  G  R  R  E  G  G  R  E  G  G  R  K  A  E  G  G  R  R  G  E  G  G  R
```

5,789,234

EXPRESSION SYSTEMS FOR AMIDATING ENZYME

RELATED APPLICATIONS

This application is a continuation-in-part of U.S. application Ser. No. 086,161 filed Aug. 14, 1987. The entire disclosure of the above-identified parent application is incorporated herein by reference.

BACKGROUND OF THE INVENTION

This invention relates to the production of alpha-amidating enzymes through recombinant DNA techniques, and particularly to expression vectors and hosts capable of expressing alpha-amidating enzyme in high yields and at recoverable high purity.

The intracellular processing (cleavage and/or functional group modification) of precursor forms of native proteins following their translation from nucleic acid coding sequences has been clearly documented.

In general, mammalian cells and other eukaryotes can perform certain post-translational processing procedures, while prokaryotes cannot. Certain prokaryotes, such as *E. coli*, are widely employed as hosts for the production of mammalian proteins via recombinant DNA (rDNA) technology because they can be readily grown in batch fermentation procedures and because they are genetically well-characterized. However, many mammalian proteins require some type of post-translational processing, and if these proteins are produced by genetic engineering of *E. coli*, for example, the post-translational processing must often be accomplished by using complex, in vitro chemical procedures which are cost-prohibitive for large-scale production applications.

One type of processing activity involves the specific amidation of the carboxyl-terminal amino acid of a peptide or protein. Many naturally-occurring hormones and peptides contain such a modification, which is often essential if the protein is to be biologically active. An example is calcitonin, where the substitution of a non-amidated proline residue for the a-rideted proline of the native form results in a 3,000-fold reduction in biological activity. Other biological peptides requiring post-translational amidation for full activity include but are not limited to growth hormone releasing factor, other calcitonins, and calcitonin gene-related peptide.

The specific amidation of the carboxyl-terminal amino acid of a protein is catalyzed by alpha-amidating enzymes. The polypeptide sequences for many important biological proteins which require amidaLion for maximal efficacy, may be manufactured, for example, by genetic engineering techniques. However, the important and sometimes essential carboxyl terminal amidation must often be performed in vitro. It is desirable to avoid costly and cumbersome chemical amidation techniques at this point, and is therefore desirable to utilize an amidating enzyme to perform the specific amidation. However, alpha-amidating enzyme is not easily obtained in nature.

The presence of amidated peptides in a particular tissue is not necessarily synonymous with high levels of alpha-amidating enzyme. For example, rat anterior pituitary tissue contains high alpha-amidating activity but no known substrates [Eipper et al, PNAS 80, 5144–5148 (1983)]. Rat posterior pituitary tissue contains amidated peptides (oxytocin and vasopressin) but has very little alpha-amidatirig activity [Eipper et al., Endo 116, 2497–2504 (1985)]. Therefore, until individual tissues are tested for alpha-amidating activity, the presence or potential levels of the enzyme cannot be anticipated.

An even greater impediment to the availability of amidating enzyme obtained from natural sources is the usually low level of purity. Amidating enzymes obtainable from natural sources are contaminated with proteolytic enzymes and other impurities. Effective recovery of amidated product is greatly hindered when these impurity-laced enzymes are used to amidate a substrate comprised of L-amino acids. The presence of proteases, in particular, may break down the substrate and/or the amidated product and/or the amidating enzyme itself. Most biologically importaant polypeptides comprise L-amino acids, and are susceptable to this proteolytic breakdown and to other amidation-hindering Impediments caused by impurities in amidaring enzyme preparations.

Because nature provides few sources, low abundance and insufficient purity of alpha-amidating enzyme, there is a need for efficient methods of mass producing alpha-amidating enzyme recoverable in high yield and at high purity.

As used herein, the terms "amidating enzyme" and "alpha-amidating enzyme" refer to any agent capable of catalyzing the conversion of a peptidyl substrate to a corresponding peptidyl amide having an amino group in place of the C-terminal amino acid of said substrate.

BRIEF DESCRIPTION OF THE INVENTION

It is an object of the present invention to provide alpha-amidating enzyme recoverable in high yields and at high purity.

It is another object of the invention to provide host organisms capable of expressing alpha-amidating enzymes recoverable in high yield and at high purity.

It is another object of the invention to provide expression vectors containing DNA sequences coding for alpha-amidating enzyme.

It is another object of the invention to provide expression vectors capable of expressing alpha-amidating enzyme in a manner wherein expressed enzyme may be easily recovered and purified to levels effective for amidation of peptidyl substrates comprising L-amino acids, for example, substrates purified from natural sources, synthesized chemically, or produced by recombinant DNA techniques.

It is another object of the invention to provide expression vectors especially suited for directing the expression of alpha-amidating enzymes in a eukaryotic host.

It is another object of the invention to provide expression vectors especially suited for directing the expression of aloha-amidating enzymes in a prokaryotic host.

It is another object of the invention to provide a means for efficient cost-effective mass production of aipha-amidating enzyme.

These and other objects are accomplished by providing a host capable of expressing a polypepotide sequence of an alpha amidating enzyme, said host comprising an expression vector which includes a transcriptional promoter followed downstream by a DNA sequence foreign to said host which encodes said amidating enzyme, said vector being capable of directing expression of polypepotides in said host.

In certain embodiments, a host is provided which is capable of expressing the polypeptide sequence of an alpha amidating enzyme, said host comprising an expression vector containing a transcriptional promoter followed downstream by a DNA sequence foreign to said host which is capable of hybridizing under stringent conditions with a DNA sequence of FIGS. 5A–5F.

In another embodiment, a host is provided which is capable of expressing the polypeptide sequence of an alpha amnidating enzyme, said host comprising an expression vector containing a transcriptional promoter followed downstream by a DNA sequence foreign to said host which is capable of hybridizing under stringent conditions with a DNA sequence of FIGS. 6A–6F.

As used herein, the term "stringent conditions" means 2×SSC (0.3M sodium chloride and 0.03M sodium citrate) at 62° C.

The present invention also provides expression vectors for directing expression of alpha-amidating enzyme in both prokaryotic and eukaryotic systems. For example, an expression vector is provided which is capable of directing, in a prokaryotic host, the expression of a polypeptide sequence of an alpha amidating enzyme, said vector comprising a transcriptional promoter followed downstream by a first DNA sequence having an amidating enzyme-coding region, said first sequence being sufficiently homologous to a natural DNA sequence for expressing natural amidating enzyme to undergo hybridization with said natural sequence under stringent conditions, and said first sequence including an initiating methionine codon within about 50 nucleotides of the start of said enzyme-coding region.

Likewise, an expression vector is provided, in another embodiment of the invention, which is capable of directing the expression of a polypeptide sequence of an alpha-amidating enzyme in a eukaryotic host, said vector comprising a transcriptional promoter followed downstream by a first DNA sequence having an amidating enzyme-coding region, said first sequence being sufficiently homologous to a natural DNA sequence for expressing natural amidating enzyme to undergo hybridization with said natural sequence under stringent conditions, and said first sequence including a stop codon upstream from a sequence which would otherwise code for a membrane spanning domain.

This first sequence should be followed by a sequence specifying the addition of poly A to the messenger RNA generated by transcription from said promoter.

As used herein, the term "membrane spanning domain" is a DNA sequence which, as determined by the test of Kyte & Doolittle, *J. Mol. Biol.*, Vol. 157, pp. 105–132 (1982) (the entire disclosure of which is hereby incorporated by reference), codes for an amino acid sequence of sufficient hydrophobicity, length, structural character, and the like to become fixed in the membrane. For example, this may occur as a protein is synthesized on a membrane-bound ribosome or, alternatively, the amino acid sequence coded by the membrane spanning domain may become associated with other areas of the protein of which it is a part, such that the sequence becomes inserted into the hydrophobic environment of the membrane post-translationally. Membrane-spanning domains are discussed in more detail in Von Heine, *Seauence Analysis in Molecular Biology: Treasure Trove or Trivial Pursuit*, pp. 81–121 (Acad. Press 1987), the teachings of which are hereby incorporated by reference.

The base numbers utilized herein are the numbers specifically stated for any DNA sequence expressly set forth together with base number references. For all sequences for which base numbers are not expressly assigned herein, the bases shall be consecutively numbered with base number 1 being the first base of the first codon that is expressed by the sequence being discussed, and the amino acid numbers are consecutively numbered with the first being the amino acid expressed by bases 1–3.

BRIEF DESCRIPTION OF THE DRAWINGS

FIG. 3 is Coomassie Blue-stained SDS-PAGE electrophoretogram of the insoluble protein fraction from *E. coli* JM105 carrying the plasmids indicated (which have the characteristics set forth in Example 1) when cultured with (+) or without (−) IPTG added to the growth medium (C=insoluble proteins of *E. coli* JM105 carrying pKK233-2).

FIG. 4 is a Western Blot of the gel shown in FIG. 3 wherein, following protein transfer to nitro cellulose, the filter was treated with rabbit anti ∝AE antisera and the alkaline phosphatase-connugated anti rabbit Ig, followed by chromogenic sibstrate for the alkaline phosphatase.

FIG. 5(A–F) is a cDNA sequence encoding an α-amidating enzyme in accordance with the invention (referred to herein as "Type A") The encoded amino acid sequence is also shown. Successive portions of the DNA sequence (and where applicable, the amino acid sequence) are set forth on FIGS. 5A–5F, respectively.

FIG. 6(A–F) sets forth another cDNA sequence encoding an α-amidating enzyme in accordance with the invention (referred to herein as "type B"). The encoded amino acid sequence is also shown. consecutive portions of the DNA seqiuence, and of the amino acid sequence, are shown in FIGS. 6A–6F, respectively.

DETAILED DESCRIPTION OF PREFERRED EMBODIMENTS

Figure 1:
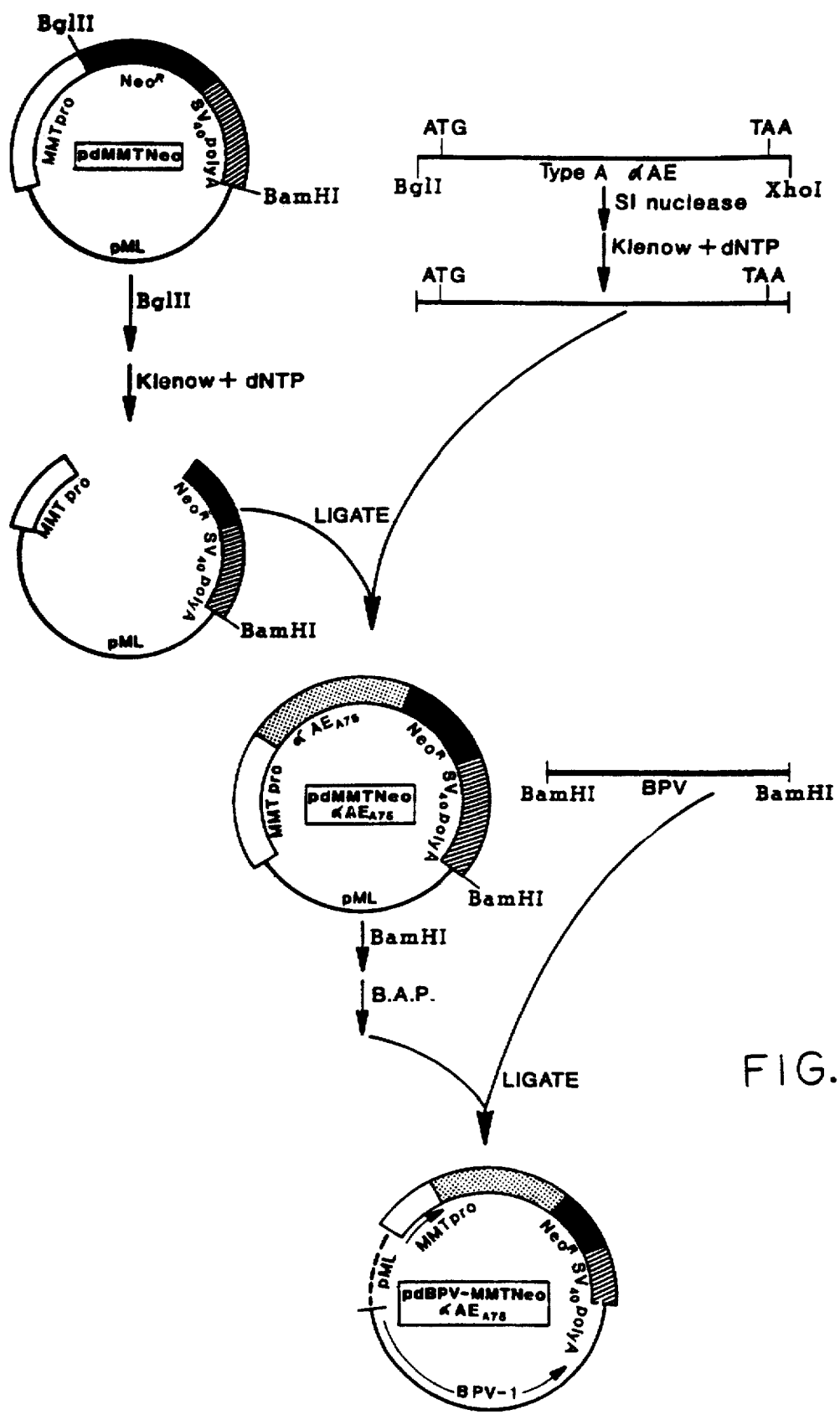
FIG. 1 is a flow chart for construction of a mammalian expression vector for alpha-amidating enzyme.

In accordance with the invention, expression vectors suitable for prokaryotic systems and expression vectors suitable for eukaryotic systems are prepared. DNA encoding amidating enzyme useful in these vectors may be isolated as taught in the parent U.S. patent application hereto, (Ser. No. 086,161 filed Aug. 14, 1987 priority of which has been claimed and the entire disclosure of which has been incorporated herein by reference). Alpha-amidating enzymes have been isolated from rat fron a rat cell line, and purified to homogeneity as taught in the above-identified parent application and in grandparent application Ser. No. 655,366 filed Sep. 27, 1984, now issued as U.S. Pat. No. 4,708,934, priority of which has been claimed and the entire disclosure of which has been incorporated herein by reference. Amino acid sequences have been determined for the purified alpha-amidating enzyme, and these sequences have been used to project a variety of oligonucleoteide probes which have been radiolabelled and utilized for isolating cDNAs for amidating enzyme.

The isolated cDNAs have been used to screen libraries prepared, for example, from the total RNA of rat medullary thyroid carcinoma tissues, their derived cell lines or frorii cell lines known to produce amidating enzyme, for example, biological deposit ATCC 75168 (in Vitro International, Linthicum, Md.) (Rat MTC tissue) or derived cell line ATCC CRL 10919. Total RNA was prepared and Poly-A RNA was selected with oligo DT cellulose. cDNAs were prepared by well known methods utilizing first reverse transcriptase and then a DNA polymerase. The cDNA was used to generate cDNA libraries in the vector λgt 11 and the recombinant DNA's were packaged in vitro to form infectious bacteriophage particles.

Extracts for packaging are commercially available for examrple from Promega Biotech or Clontech Laboratories or can be prepared according to methods well-known in the art. The phage were screened with radlolabelled oligonucl eotide probes prepared as set forth above. Screening for bacteriophage containing alpha aitidati.ng enzyme cDNA ("AE cDNA") was accomplished by plating samples of bacteriophage and lifting the phage onto nitrocellulose filter discs. Hybridization with two or more radiolabelled AE-specific oligonucleotide probes conferred specifilcilty.

Oligonucleotide probes denoted AE4, AE5, AE8 and AE9 at paces 61–64 of parent U.S. application Ser. No. 086,161 (filed Aug. 14, 1987) are especially preferred when screening libraries prepared from biological deposit ATCC CAL 10919 identified above.

Analysis o f the AE cDNAs from many bacteriophage isolated by the above oligonucleotide hybridization screening procedures indicated that the cDNAs could be separated into a plurality of distinct types. The structure of one type is shown in FIGS. 5A–5F ("Diagram A" or "Type A sequence") where the nucleotides have been numbered with base 1as the first base of the codon for the initiator methionine. Below the nucleotide sequence is given the single letter amino acid code for translation of the gene seauence into protein. Numbers in parentheses at the end of lines indicate amino acid numbers.

Another type of CDNA sequence isolated by the oligonucleotide hybridization screening set forth above is represented by FIGS. 6A–6F ("Diagram B" or "Type B sequence") where the numbering and other conventions are the same as those stated for FIGS. 5A–5F Applicants have utilized cDNAs isolated in the above manner for constructing both prokaryotic and eukaryotic expression vectors and a number of hosts have been transfected with these vectors for effective expression of alpha-amidating enzyme.

In preferred embodiments of the invention, applicants have made novel modifications to the foregoing cDNAs in order to optimize not only expression, but also recovery of amidating enzyme. The nature and extent of modification may vary with the host and/or vector selected. For example, applicants insert, in preferred embodiments, a stop codon upstream from a sequence which would otherwise code for a membrane spanning domain. The presence of these membrane spanning domains may be undesirable for a recombinant DNA expression system since they may cause the expressed protein to be membrane associated and possibly inactive in the host organism or cell line. Examples of membrane spanning domains appear in the two cDNA examples set forth in diagrams A and B above (about bases 2275–2355 of the sequence shown in diagram A and about bases 2587–2667 of the sequence shown in diagram B). The cDNAs of diagrams A and B are substantially identical on the amino side of these transmembrane domains with the exception of what appears to be an intron region from base 1178 through base 1492 of the type B cDNA.

The cDNAs of diagrams A and B above encode protein products of approximately 94 and 105 kD, respectively. Both of these proteins are larger than mature, active enzymes that have been purified from animal tissue extracts or cell line secretions. Each of these primary translation products are pre-proerzymes that contain membrane-spanning domains in the C-terminal one-third of the ccding sequence. It is preferred that the stop codon be placed so that the expressed protein has a molecular weight of about 75 kd for when expressed by the cDNA of diagram A (i.e. the stop is placed between bases 2025 and 2275) and 87 kD when expressed by the cDNA of diagram B(i.e., the stop is placed between about bases 2340 and 2690).

For cytoplasmic expression of the mature alpha ainidating enzyme in E. coli, for example, it is preferred that the gene sequences that encode the natural secretory signal sequence be removed, that an initiation codon be placed within about 50 nucleotides of the gene sequences encoding the start of the mature protein corresponding to alpha-amidatinq enzyme, and that the gene sequences encoding the membrane spanning domain in the C-terminal region not be translated. The initiating codon is of course in-frame with the sequence which encodes the enzyme and, in some preferred embodiments, is upstream from the region, sometimes immediately upstream.

When the AE cDNA was expressed in E. coli, it was discovered that the natural gene sequence contained a cryptic E. coli ribosome binding site ("RBS") and initiation codon internal to the natural initiation sequences. This resulted in the production of an N-terminally truncated amidating enzyme protein. While this did not prevent the production of the desired product in E. coli, the coexistence of the correctly initiated and internally initiated products complicates the processing and purification of the recombinant product to a useful form and is therefore undesirable. To eliminate the unexpected, undesired product, it was necessary to eliminate either the ribosome binding site, the internal initiation codon or both of these.

For example, in certain preferred embodiments of the invention, a valine codon which, In prokaryotic systems, codes an initiating methionine, is altered by a point mutation to an equivalent non-initating valine codon at bases 661–663 (of the cDNAs of either diagram A or B). In lieu of this point mutation or in addition thereto, applicants, in other preferred embodiments, delete or substantially modify any region coding for a ribosome binding site whicrh occurs just upstream of an internal initiation site, and more preferably any internal ribosome binding site whenever one may occur. These modifications are made to substantially eliminate internal initiation such that the protein expressed because of internal initiation is not observed as a separate band following electrophoresis.

To obtain expression of secreted, active alpha amidating enzyme protein, from a recombinant eukaryotic host cell line it was necessary to remove the gene sequences encoding the transmembrane domain found in the C-terminal region of the natural gene sequences. For the type A CDNA this has been done by truncation of the protein coding region through introduction of a stop codon at or near to where the natural amidating enzyme is post-translationally processed in some natural systems as explained in detail below. For the type B CDNA this has also been done by introducing a new stop codon in the region of the enzyme protein where the natural type B amidating enzyme is post-translationally processed (see below). This should not be taken to exclude the possiblity that in some host cell systems it may be preferable to express the entire naturally occuring gene sequences. Because the type B cDNA contains sequences with the characteristics of an unprocessed intron there may be a difficulty in expressing this cDNA in some eukaryotic host cells. These cells may not efficiently produce an mRNA from the type B gene due to the presence of the paired splice donor and acceptor sites. ElimLnation of the acceptor site might therefore be necessary to allow for efficient expression of type B AE cDNA We have discovered that the carboxyl end of the naturally occurring 75 kD alpha amidating enzyme protein occurs beyond amino acid position 709 (814 of type B). To produce the 75 kD protein (87 kD of type B) in a recombinant DNA host cell, a stop codon has been introduced into the cDNA by mutation of the codon for the lysine of amino acid position 716 (821 of type B). This modification has been made using oligonuclectide directed site specific mutagenesis. Such mutagenesis can be accomplished in a variety of ways. The methods have been reviewed extensively in the molecular biology literature. The general method that we have used was described by Taylor, J. W. et al. (1985), Nucl. Acids Res., 13: 8749–8764; Taylor, J. W. et al. (1985), Nucl. Acids Res., 13: 8764–8785; Nakamaye, K. and Eckstein, F. (1986). Nucl. Acids Res., 14: 9679–9698. The reagents needed to practice theis method are available in the form of a mutagenesis kit from Amersham Corporation.

The mutation of the sequence that we have produced changes the AAA lysine codon to a TAA stop codon. The oligonucleotide used for the mutagenesis incorporated this change but was otherwise identical in sequence to the naturally occurring cDNA sequence for the respective enzyme (type A or type B) being mutated.

We have also discovered that a naturally occurring shortened torm of the alpha amidating enzyme protein is produced by processing of the type B protein at the internal region of the protein that is unique to the type B enzyme protein. This results in an enzyme product that is approximately 43 kD in molecular masse Without intending to be bound by theory, it is believed that the DNA sequence upstream from the intron region is sufficient to code for a polypeptide capable of exhibiting significant alpha-amidating activity. Accordingly polypeptides which are easy to recover and which are capable of expressing alpha-amidatina activity may be encoded by cDNAs which are significantly truncated by placement of a stop codon somewhere in the intron region of type B cDNA in just before or after the corresponding location where this intron is missing from TYPE A cDNA. Preferred truncation results from placement of a stop codon within about 30 bases of the beginning of the of the intron region, preferably immediately downstream therefrom. To enable the production of one preferred short form of alpha amidating enzyme protein in recombinant host cells, a modified cDNA is created having a stop codon in place of the lysine codon at amino acid position 436 of the type B cDNA. This mutation was accomplished by oligonucleotide directed site specific mutagenesis of the type B AE cDNA.

While the shortening of the amidating enzyme protein by introduction of the stop codon at amino acid position 436 of the type B cDNA gives a protein that most closely approximates the one produced naturally by proteolytic cleavage of the primary translation product (or some other cleavage intermediates in the biosynthetic pathway), a further shortening of the amidating enzyme protein may also result in production of an active product in recombinant DNA host cells. We have modified the AE cDNA in several other ways to create such shorter forms of protein. In one example, we have used oligonucleotide directed site-specific mutagenesis to convert a tyrosine codon at amino acid position 396 of the type B cDNA to a stop codon. This change will result in a protein that is approximately 39 kD when the cDNA is translated and processed. In a second case, we have utilized the naturally occuring Bam H1 enzyme recognition site of the type B cDNA to introduce a stop codon by linker mutagenesis. This method is well known in molecular biology and simply involves the cleavage of the cDNA followed by ligation to a double stranded synthetic linker fragment that is complimentary to one end of the cleaved cDNA and that introduces an in frame stop codon just beyond the cleavage site. We have used an oligonucleotide fragment with the following sequence to accomplish this modification:

$^5$'GATCCACTAATGATCA$^3$'
$_3$'GTGATTACTAGTTCGA$_5$'

This linker introduces a stop codon following the histidine codon at amino acid 469. Translation and processing of the cDNA once it has been modified in this fashion results in the synthesis of a protein of approximately 46 kD.

Preferred placement of a truncating stop codon is within about 15 bases of a DNA sequence which codes for consecutive basic residues (usually a Lys—Lys) and especially immediately upstream therefrom. Without intending to be bound by theory, it is believed that the natural polypeptide coded by the cDNAs of type B is processed, during post-translational modifications which occur during natural expression of amidatIng enzyme, at or near such consecutive basic residues, for example, the consecutive lysines coded within the intrcn region of the cDNA of diagram B. Even when the inserted stop codon-s are not intended to truncate the expressed polypeptide in the above-described manner, it is preferred that the inserted stop codon be placed within about 20 bases, and preferably immediately upstream from, DNA sequences coding for consecutive basic amino acid residues. insertion of stop codons at these positions will likely result in expression of a polypeptide resembling certain natural amidating enzymes after they have undergone post-translational processing.

For cytoplasmic expression in prokaryotic systems, any signal sequence coding regions (for example, the first bases of both the type A and type B cDNAs diagrammed previously) are preferably eliminated and a methionine initiator codon is inserted within about 50 nucleotides of the beginning of the region which codes for amidating enzymes.

An alternative embodiment for prokaryotic expression eliminates any coding sequences for signal sequence or proenzyme sequence and inserts an initiator methionine codon within about 50 nucleotides of the beginning of the region which codes for amidating enzyme. In many natural AE cDNAs, this corresponds to the beginning of the region which encodes ser-x-ser (X being phe or leu). See, for example, bases 124 to 132 of the sequence for type A or type B cDNA. In some embodiments secretion of alpha amidating enzyme may be desirable, in this case it is preferable to retain the signal sequence coding regions, or alternatively to replace them with heterologous sequences that can serve the same function, for example, the signal sequences of the bacterial OMP A protein.

It will be readily apparent to those skilled in the art that numerous mutations and truncations of the DNA sequences set forth herein for encoding amidating enzyme are possible within the scope of the invention and that such modified sequences would code for polypeptides capable of functioning as amidating enzymes. Accordingly, applicants claims should be construed to include all functional equivalents of DNA sequences, expression vectors and host cells specifically set forth.

Examples of prokaryotic expression vectors which may desirably be modified to include DNA sequences encoding amidating enzyme in accordance with the invention include but are not limited to pKK233-,pKK322-2, pPROK-1, pkT279,280,287, pPL lambda, pYEJ001, pKC30, pPROK-C, all commercially available. Prokaryotic hosts which may be transfected with expression vectors in accordance with the invention include but are not limited to C600, LE392, RR1, DH1, SF8, all commerically available.

Eukaryotic expression vectors which may desirably be modified to include DNA sequences encoding amidating enzyme in accordance with the invention include but are not limited to pMAMNeo, pdBPVMMTNeo, pRSV, peuK-C1, pCH110, all commerically available. Appropriate yeast vectors may also be used. Preferred eurokaryotic hosts may be transfected with expression vectors in accordance with the invention include but are not limited to ATCC deposit CRL 10919, Hela, CV1, C127, CHO (Chinese Hamster Ovary) and COS.

EXAMPLE 1

Expression of Alpha Amidating Enzyme Proteins in E. coli

Figure 2:
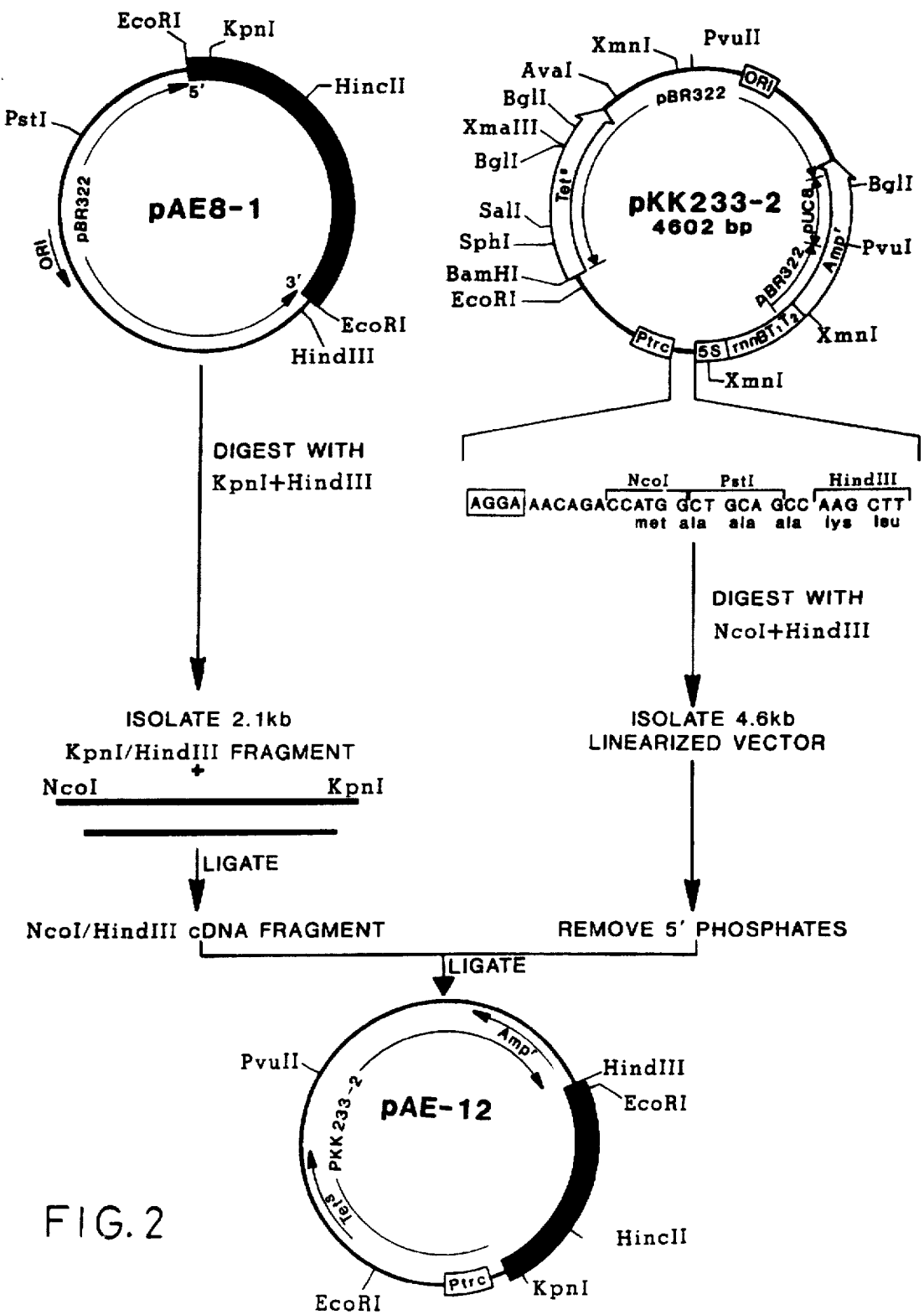
FIG. 2 is a flow chart for construction of a prokaryotic expression vector for alpha-amidating enzyme.

In order to express alpha amidating enzyme in *E. coli* (see the flow chart of FIG. 2), a cDNA fragment having the sequence set forth in diagram A, above, was digested with KpnI and Hind III and the fragment of about 2.1 kb was isolated. To build back a amino terminus corresponding to a natural mature enzyme, an oligonucleotide linker with the sequence $5'$CATGTCATTTTCCAATGAATGCCTTGGTAC$3'$
$3'$AGTAAAAGGTTACTTACGGAAC$5'$.

was ligated to this DNA fragment. The resulting fragment contained one Nco I compatible sticky-end and one Hind III sticky end. The *E. coli* expression vector pK233-2was obtained commercially from Pharmacia and digested with restriction enzymes Nco I and Hind III. The large linear fragment was isolated and ligated to the linker adapted cDNA fragment. The ligation mixture was used to transform competent *E. coli* JM105. Transformants were selected by ampicillin resistance and the clones isolated were analyzed for the recombinant plasmid by restriction enzyme and DNA sequence analysis to confirm the structure of the expression vector (hereafter "pAE12") that they contained. The expression vector contains the hybrid trp-lac promoter which is repressed by the lac repressor and inducible by treatment of the cells with isopropylthiogalactoside (IPTG). Upstream from the initiator methionine tlhe vector also contains the sequences of a strong ribosome binding site.

To obtain expression of the alpha amidating enzyme in the *E. coli*, the recombinant cells were grown with shaking in LB-broth at 37° C. to an $CD_{600}$ of 0.4. IPTG was added to the culture to a final concentration of lmM and the growth was allowed to continue at 37° C. with shaking for three to five hours. Cells were collected by centrifugation of the culture and the supernatant was discarded. The cells were resuspended in buffer containing a coctail of protease inhibitors, treated with lysozyme and then sonicated to lyse the cell membranes. The lysates were centrifuged at 12,000×g to separate the soluble and insoluble fractions of the cells. Each fraction was analyzed by SDS-PAGE and protein staining. The alpha amidating enzyme protein was readily identified as an IPTG inducible product in the insoluble protein fraction. Since the initial expression plasmid did not contain a stop codon specified by the alpha amidating enzyme gene sequences, the inducible product formed contains sequences specified by downstream vector DNA fused to the C-terminal of the alpha amidating enzyme protein sequences. In addition, the induced insoluble protein also contained a smaller amidation enzyme specific protein that represented a product formed by internal initiation of protein synthesis at a cryptic RBS and initiation codon (amino acid position 221 of the alpha amidating enzyme sequence).

To remove the unwanted sequences from the C-terminal portion of the expressed product, a mutation of the lysine codon at position 716 of the type A sequence was made to generate a TAA stop codon at this position. The mutated cDNA was then digested with Kpn I and Eco R1 and used to replace the original Kpn I-Eco R1 fragment in the initial expression vector pAE12. In a similar fashion, the type B cDNA sequences were mutated at the comparable position (amino acid 821) to create a stop codon and the Kpn I-Eco R1 fragment from the mutated type B cDNA was used to replace the corresponding fragment in pAE12. The two expression plasmids so created pAE24 (type A) and pAE25 (Type B) were then used to transform JM105. The resulting strains were cultured for expression as was done previously for pAE12-containing strains. The pAE24 was found to produce two IPTG inducible, insoluble proteins of approximately 75 kD and 55 kD while the pAE25 was found to produce two IPTG inducible insoluble proteins of about 87 kD and 67 kD. Again, the small protein in each of these pairs represents the unwanted amino-terminally truncated product from either the type A or type B cDNA.

To eliminate the initiation of protein synthesis at the cryptic internal ribosome binding site and initiation codon (amino acid position 221) the GTG start codon, (GTG can serve as an initiator met codon in bacteria), was converted to a GTT codon that cannot initiate protein synthesis but which still encodes the valine that is normally found at this position in alpha amidating enzyme proteins encoded by natural genes. When the mutated region of the cDNA was substituted for the natural sequence in the expression vectors pAE24 and pAE25, two new vectors were created, pAE31 and pAE32. Transforming *E. coli* JM105 with these modified expression vectors and testing protein production from the resulting recombinant strains indicated that this mutagenesis was effective in eliminating the unwanted internal initiation. The IPTG induced product from the host cells carrying pAE31 was found to be 75 kD while that from cells transformed with pAE 32 was found to be 87 kD.

Since we have found that naturally occurring amidating enzyme from type B cDNA is post-translationally processed to give proteins of approximately 43 kD, we have prepared a series of mutations in type B AE cDNA that allows expression of proteins that terminate at or near the position where the naturally processed enzyme ends. Two of these mutations were prepared by oligonucleotide mutagenesis while a third was created by adapter-linker mutation as indicated above. When cDNAs carrying these mutations were used to replace the corresponding segments of pAE32, transformed into JM105 and analyzed for protein production in experiments similar to those described above, truncated alpha amidating enzyme proteins were detected. With a mutation at amino acid position 396 of type B cDNA changing a natural tyrosine codon to a stop codon (pAE36), a 39 kD enzyme protein was found while a linker mutagenesis that ended translation at the histidine codon of amino acid 464 resulted in a vector, pAE51, which produced a recombinant alpha amidating enzyme protein of 46 kD following transformation and induction of *E. coli* JM105.

All of recombinant alpha amidating enzyme proteins produced in *E. coli* described above were found to segregate with the insoluble fraction of the cell extracts. The enzymes could be rendered soluble and active by treatment with 8M urea followed by rapid dilution in 50 mM Tris-HCl pH7. When *E. coli* JM105 carrying pAE12 was grown and induced with IPTG as described, the alpha amidating enzyme proteins were present at levels of at least 30 mgs per liter of bacterial culture.

Representative samples of the induced insoluble protein produced in *E. coli* carrying AE expression plasmids are shown in FIGS. 3 and 4.

EXAMPLE 2

Generation of mammalian expression vector ud BPV-MMTNEO-AE$_{A75}$

To generate a mammalian expression vector which expresses and constitutively secretes 75 kD type A alpha amidating enzyme from mammalian cells (see the flow chart of FIG. 1), the following was performed:

1) The intermediate expression vector pdMMTNeo (commercially available from American Type Culture Collection) (as shown) was digested with Bgl II. The linear form was isolated and purified.

2) The recombinant type A cDNA containing the full prepro sequence and an artificial stop codon TAA at position 2146–2148 was isolated by sequential digestion with Bgl I and Xho I. The fragment corresponding to alpha amidating enzyme was then isolated and purified.

3) The insert (type A alpha amidating enzyme) and vector (pdMMTNeo) were mixed and the corresponding ends were made flush using the Klenow fragment of DNA polymerase I. The 5' protruding segments were filled in with added dNTP, and the 3' protruding segments were digested back to produce a flush end (alternatively sequential S1 nuclease and Klenow+dNTP could be utilized for producing flush ends). The flush ended molecules were then ligated for 16 hours at 15° C.

4) The ligated material was then transformed into E. coli RRI. Recombinant clones were selected in the presence of 50 ug/ml ampicillin. The orientation of the insert in the recombinant clones was verified using a battery of restriction enzymes. One clone which was referred to as pdMMTNeo $\propto$-AE$_{A75}$ (clone 11) was determined to have the type A cDNA in the correct orientation with respect to the MMT promoter.

5) Plasmid DNA from recombinant pdMMTNeo $\propto$-AE$_{A75}$ (clone 11) was digested with BamHI. The linearized vector was isolated and purified and then treated with bacterial alkaline phosphatase (B.A.P.) for 2 hours at 37° C. to remove 5' phosphates. The BPV-1 genome was isolated and purified following B and BamHI digestion of the vector pdBPVMMTNeo. This BamHI fragment of BPV-1 DNA, which is approximately 8.0 kb, was then ligated to the BamHI linearized and B.A.P. treated pdMMTNeo $\propto$AE$_{A75}$ vector, for 3 hours at 14° C. After the ligation mixture was transformed into E. coli RR1, the recombinant clones were selected on 50 ug/ml Ampicillin LB agar plates. The recombinant plasmids were analyzed for BPV DNA and were also analyzed for type A AE cDNA. Restriction mapping revealed that clone 21 was approximately 17 kb and produced a restriction map as expected. This expression plasmid was then used for expression of $\propto$AE$_{A75}$ in mouse C127 cells.

6) Mouse C127 cells were transfected with 20 ug of pdBPV-MMTNeo $\propto$AE$_{A75}$ by the standard CaPO$_4$ precipitation technique. Approximately 2 weeks post transfection, transformed foci were individually picked and grown in growth media containing the antibiotic G418. When cells were grown to a sufficient capacity in Dulbecco's Modified Eagle Medium plus 10% fetal calf serum, the clones were assessed for the ability to secrete Alpha Amidating Enzyme by measuring the enzymatic activity in the conditioned cell culture media, as well as by measuring the alpha amidating enzyme immunoreactivity in the medium using standard radiolabelling and immunoprecipitation techniques. Clones secreting active, immunoreactive 75 kD alpha amidating enzyme were expanded to large numbers of cells (switched to cell culture medium with reduced serum and therefore reduced level of exogenous protein) and are in use to produce large quantities of active recombinant enzyme from the cell conditioned media.

The terms and descriptions used herein are embodiments set forth by way of illustration only, and are not intended as limitations on the many variations which those of skill in the art will recognize to be possible when practicing the present invention, as defined by the following claims.

What is claimed is:

1. A host cell transformed or transfected with an expression vector comprising a first DNA sequence which hybridizes under stringent conditions with a natural DNA sequence shown in FIGS. 5A–5F.

2. A host cell transformed or transfected with an expression vector comprising a first DNA sequence which hybridizes under stringent conditions with a natural DNA sequence.

3. The host cell according to claim 1 or 2, wherein said first DNA sequence contains a stop codon 5' of a membrane spanning domain.

4. The host cell according to claim 3, wherein said stop codon is 5' of a consecutive lysine coding region.

5. The host cell of claim 1, wherein said expression vector comprises a promoter sequence for driving transcription of said first DNA sequence, followed by said first DNA sequence, followed by a selectable marker, followed by a sequence for encoding canonical poly A addition sequences and transcription termination sequences.

6. The host cell of claim 5, wherein said first DNA sequence contains a stop codon following the bases which code for amino acid 715.

7. The host cell of claim 6, wherein said expression vector is pdBPCMMTNeO, said promoter is a metallothionin promoter, and said selectable marker is a gene coding for neomycin resistance.

8. The host cell of claim 6, wherein said stop codon results from a change in the codon at positions 2146–2148 said change converting said condon which encodes the amino amid at position 716 to a translational stop signal.

9. The host cell of claim 8, wherein said expression vector is pdBPCMMTNeO, said promoter is a metallothionin promoter, and said electable marker is a gene coding for neomycin resistance.

10. The host cell of claims 5, 6 or 9, wherein said cell is a mouse C127 cell.

11. The host cell of claim 5, wherein said vector is a pSV-derived vector.

12. The host cell of claim 5, wherein said selectable marker is a dihydrofolate reductase gene.

13. The host cell of claims 11 or 12, wherein said host cell is a chinese hamster ovary cell.

14. The host cell of claim 2, wherein said expression vector comprises a promoter sequence for driving transcription of said first DNA sequence, followed by said first DNA sequence, followed by a selectable marker, followed by a sequence for encoding canonical poly A additional sequences and transcription termination sequences.

15. The host cell of claim 14, wherein said first DNA sequence contains a stop codon following the bases which code for amino acid 435.

16. The host cell of claim 15, wherein said expression vector is pdBPCMMTNeO, said promoter is a metallothionin promoter, and said selectable marker is a gene coding for neomycin resistance.

17. The host cell of claim 15, wherein said stop codon results from a change in the condon at positions 1306–1308, said change converting said condon which encodes the amino acid at position 436 to a translational stop signal.

18. The host cell of claim 17, wherein said expression vector is pdBPCMMTNeO, said promoter is a metallothionin promoter, and said selectable marker is a gene coding for neomycin resistance.

19. The host cell of claims 14, 15 or 18, wherein said cell is mouse C127.

20. The host cell of claim 14, wherein said vector is a pSV-derived vector.

21. The host cell of claim 14, wherein said selectable marker is a dihydrofolate reductase gene.

22. The host cell of claim 21 or 22, wherein said host cell is a chinese hamster ovary cell.

23. An expression vector for directing the expression of a polypeptide sequence of an alpha amidating enzyme in prokaryotic cells, said vector comprising a first DNA sequence having an amidating enzyme-coding region, said first DNA sequence being sufficiently homologous to a natural DNA sequence for encoding natural amidating enzyme to undergo hybridization with said natural sequence under stringent conditions, wherein said natural DNA sequence is shown in FIGS. 5A–5F.

24. The expression vector of claim 23, wherein said first DNA sequence contains a stop codon located between base 2025 and 2275.

25. An expression vector for directing the expression of a polypeptide sequence of an alpha amidating enzyme in prokaryotic cells, said vector comprising a first DNA sequence having an amidating enzyme-coding region, said first DNA sequence being sufficiently homologous to a natural DNA sequence for encoding natural amidating enzyme to undergo hybridization with said natural sequence under stringent conditions, wherein said natural DNA sequence is shown in FIGS. 6A–6F.

26. The expression vector of claim 25, wherein said first DNA sequence contains a stop codon is located between bases 1148 and 1492.

27. The expression vector of claim 26, wherein said stop codon is located between bases 1148 and 1208.

28. The expression vector of claim 25, wherein said first DNA sequence contains a stop codon is located between bases 2340 and 2690.

29. An expression vector for directing the expression of a polypeptide sequence of an alpha amidating enzyme in eukaryotic cells, said vector comprising a first DNA sequence having an amidating enzyme-coding region, said first sequence being sufficiently homologous to a natural DNA sequence for expressing natural amidating enzyme to undergo hybridization with said natural sequence under stringent conditions, and said first sequence including a stop codon 5' of a membrane spanning domain, wherein said natural DNA sequence is shown in FIGS. 5A–5F.

30. The expression vector of claim 29, wherein said stop codon is located between bases 2025 and 2075.

31. An expression vector for directing the expression of a polypeptide sequence of an alpha anidating enzyme in eukaryotic cells, said vector comprising a first DNA sequence having an anidating enzyme-coding region, said first sequence being sufficiently homologous to a natural DNA sequence for expressing natural amidating enzyme to undergo hybridization with said natural sequence under stringent conditions, and said first sequence including a stop codon 5' of a membrane spanning domain, wherein said natural DNA sequence is shown in FIGS. 6A–6F.

32. The expression vector of claim 31, wherein said stop codon is located between bases 1148 and 1492.

33. The expression vector of claim 31, wherein said stop codon is located between bases 1148 and 1208.

34. The eukaryotic expression vector of claim 31, wherein said vector is formed by ligating said first DNA sequence into an expression system selected from the group consisting of pdBPVMMTNeo, pSV$_2$, pRSV, pMAMNeo, peuK-C1, pCH110, and derivatives of the foregoing.

35. The expression vector of claim 31, wherein said stop codon is located between bases 2340 and 2690.

36. A host cell for expressing the polypeptide sequence of an alpha amdiating enzyme, said host cell transformed or transfected with an expression vector containing the DNA sequence shown in FIGS. 5A–5F.

37. A host cell for expressing the polypeptide sequence of an alpha amidating enzyme, said host cell transformed or transfected with an expression vector containing the DNA sequence shown in FIG. 6.

38. A method of manufacturing an amidated peptide comprising contacting a precursor of said peptide with a peptidylglyuine alpha-amidating monooxygenase expressed from a host cell transformed or transfected with an expression vector comprising a first,DNA sequence which hybridizes under stringent conditions with a natural DNA sequence that is shown in FIGS. 5A–5F or FIGS. 6A–6F.

* * * * *